US00PP12961P2

(12) United States Plant Patent
Vanspronsen

(10) Patent No.: US PP12,961 P2
(45) Date of Patent: Sep. 17, 2002

(54) CHRYSANTHEMUM PLANT NAMED 'APRICOT CHERIE'

(75) Inventor: Simon Vanspronsen, Niagara-on-the-Lake (CA)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/829,490

(22) Filed: Apr. 11, 2001

(51) Int. Cl.[7] ..... A01H 5/00

(52) U.S. Cl. ..... Plt./297

(58) Field of Search ..... Plt./297

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Apricot Cherie', characterized by its uniform, rounded and outwardly spreading plant habit; freely branching growth habit; small dark green foliage; uniform flowering response; early and freely flowering habit; small daisy-type inflorescences; soft pink-colored ray and bright yellow-colored disc florets.

2 Drawing Sheets

BACKGROUND OF THE INVENTION

The present Invention relates to a new and distinct cultivar of Chrysanthemum plant, botanically known as *Chrysanthemum×morifolium* and hereinafter referred to by the name 'Apricot Cherie'.

The new Chrysanthemum was discovered as a naturally-occurring whole plant mutation of the Chrysanthemum cultivar Yellow Cherie, disclosed in U.S. Plant Pat. No. 9,713.

The new Chrysanthemum was discovered and selected by the Inventor as a single flowering plant within a population of plants of the parent cultivar in 1996 in a greenhouse in Niagara-on-the-Lake, Ontario, Canada. The selection of this plant was based on its unique ray floret color.

Asexual reproduction of the new Chrysanthemum by vegetative tip cuttings was first conducted in Niagara-on-the-Lake, Ontario, Canada in 1996. Asexual reproduction by cuttings has shown that the unique features of this new Chrysanthemum are stable and reproduced true to type in successive generations.

SUMMARY OF THE INVENTION

The cultivar Apricot Cherie has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Apricot Cherie'. These characteristics in combination distinguish 'Apricot Cherie' as a new and distinct Chrysanthemum:

1. Uniform, rounded and outwardly spreading plant habit.
2. Freely branching growth habit.
3. Small dark green foliage.
4. Uniform flowering response.
5. Typically grown as a spray-type.
6. Early flowering, eight-week response time.
7. Freely flowering habit.

8. Small daisy-type inflorescences that are about 3.7 cm in diameter.
9. Soft pink-colored ray and bright yellow-colored disc florets.

Plants of the new Chrysanthemum can be compared to plants of the parent cultivar, Yellow Cherie. In side-by-side comparisons conducted by the Inventor in Salinas, Calif., plants of the new Chrysanthemum differ from plants of the cultivar Yellow Cherie in the following characteristics:

1. Plants of the new Chrysanthemum are much larger than plants of the cultivar Yellow Cherie.
2. Plants of the new Chrysanthemum have soft pink-colored ray florets whereas plants of the cultivar Yellow Cherie have yellow-colored ray florets.

Plants of the new Chrysanthemum can be compared to plants of the Chrysanthemum cultivar Bronze Cherie, disclosed in U.S. Plant Pat. No. 9,702. In side-by-side comparisons conducted by the Inventor in Salinas, Calif., plants of the new Chrysanthemum differ from plants of the cultivar Bronze Cherie in the following characteristics:

1. Plants of the new Chrysanthemum are slightly larger than plants of the cultivar Bronze Cherie.
2. Plants of the new Chrysanthemum have soft pink-colored ray florets whereas plants of the cultivar Bronze Cherie have soft bronze-colored ray florets.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph on the first sheet comprises a side perspective view of a typical flowering plant of 'Apricot Cherie' grown a spray-type.

The photograph at the top of the second sheet comprises a close-up view of typical inflorescences of 'Apricot Cherie' grown as a spray-type.

The photograph at the bottom of the second sheet comprises a close-up view of typical inflorescences of the new Chrysanthemum (left) and 'Bronze Cherie' (right).

DETAILED BOTANICAL DESCRIPTION

In the following description, color references are made to The Royal Horticultural Society Colour Chart except where general terms of ordinary dictionary significance are used. The following observations and measurements describe plants grown and flowered during the winter in Salinas, Calif., in a fiberglass-covered greenhouse and under conditions which approximate those generally used in commercial potted Chrysanthemum production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about 14 days later. At that time, the photoinductive short day/long night treatments were started. Plants used for this description were grown as spray-types. Measurements and numerical values represent averages of typical flowering plants.

Botanical classification: *Chrysanthemum×morifolium* cultivar Apricot Cherie.

Commercial classification: Daisy-type potted Chrysanthemum.

Parentage: Naturally-occurring whole plant mutation of *Chrysanthemum×morifolium* cultivar Yellow Cherie, disclosed in U.S. Plant Pat. No. 9,713.

Propagation:

*Type.*—Terminal tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum that is typically grown as a spray-type. Stems upright and outwardly spreading; uniform, rounded crown. Freely branching, about five lateral branches develop after removal of terminal apex (pinching); dense and full plants. Moderately vigorous.

*Plant height.*—About 20.5 cm.

*Plant width.*—About 35 cm.

*Lateral branches.*—Length: About 15 cm. Diameter: About 3 mm. Internode length: About 1 cm. Strength: Strong, flexible. Texture: Pubescent. Color: 144A.

*Foliage description.*—Arrangement: Alternate. Quantity of leaves per lateral stem: About 9. Length: About 3.8 cm. Width: About 3.3 cm. Apex: Rounded, cuspidate to mucronate. Base: Attenuate to truncate. Margin: Palmately lobed, sinuses between lateral lobes divergent. Texture: Upper and lower surfaces with very fine pubescence; veins prominent on lower surface. Color: Young foliage, upper surface: 147A. Young foliage, lower surface: Close to 147B. Mature foliage, upper surface: Close to 147A. Mature foliage, lower surface: 147B. Venation, upper surface: 147A to 147B. Venation, lower surface: 147B to 146C. Petiole length: About 2.2 cm. Petiole diameter: About 2 mm. Petiole color: 147B to 146C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Typically grown as a spray-type.

*Flowering response.*—Under natural conditions, plants flower in the autumn/winter in the Northern Hemisphere. At other times of the year, inflorescence initiation and development can be induced under short day/long night conditions (at lease 13.5 hours of darkness). Early flowering; plants exposed to two weeks of long day/short night conditions followed by photoinductive short day/long night conditions flower about 49 to 53 days later when grown during the winter.

*Postproduction longevity.*—Inflorescences maintain good color and substance for about two weeks in an interior environment.

*Quantity of inflorescences.*—Freely flowering, about 7 inflorescences develop per lateral stem, or about 35 inflorescences per plant.

*Inflorescence bud.*—Height: About 4 mm. Diameter: About 6.5 mm. Color: Close to 143A.

*Inflorescence size.*—Diameter: About 3.7 cm. Depth (height): About 1.1 cm. Diameter of disc: About 1.1 cm. Receptacle diameter: About 3 mm.

*Ray florets.*—Shape: Elongated-oblong. Orientation: Initially upright, then about 80 to 85° from vertical. Aspect: Mostly flat and straight. Length: About 2 cm. Width: About 5 mm. Corolla tube length: About 3 mm. Apex: Rounded, emarginate. Base: Attenuate; short corolla tube. Margin: Entire. Texture: Smooth, glabrous, satiny. Number of ray florets per inflorescence: About 22 arranged in one or two rows. Color: When opening, upper and lower surfaces: Close to 39B to 39C, becoming close to 38A. Fully opened, upper surface: Close to 39C to 39D; becoming lighter, close to 38B to 38C; fading to close to 38C to 38D. Fully opened, lower surface: Close to 39D to 38D.

*Disc florets.*—Arrangement: Massed at center of receptacle. Shape: Tubular, elongated. Apex: Five-pointed. Length: About 6 mm. Width: Apex: About 1.75 mm. Base: About 1 mm. Number of disc florets per inflorescence: About 72. Color: Immature: 4C. Mature: Apex: 4A. Mid-section: Close to 144B. Base: 155D.

*Peduncles.*—Length: First peduncle: About 3.1 cm. Fourth peduncle: About 5.5 cm. Seventh peduncle: About 5.9 cm. Diameter: About 1.5 mm. Angle to vertical: About 45 to 50° from vertical. Strength: Wiry, flexible. Texture: Pubescent. Color: 144A.

*Reproductive organs.*—Androecium: Present on disc florets only. Anther color: 12A. Pollen: Scarce, close to 13A. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Apricot Cherie', as illustrated and described.

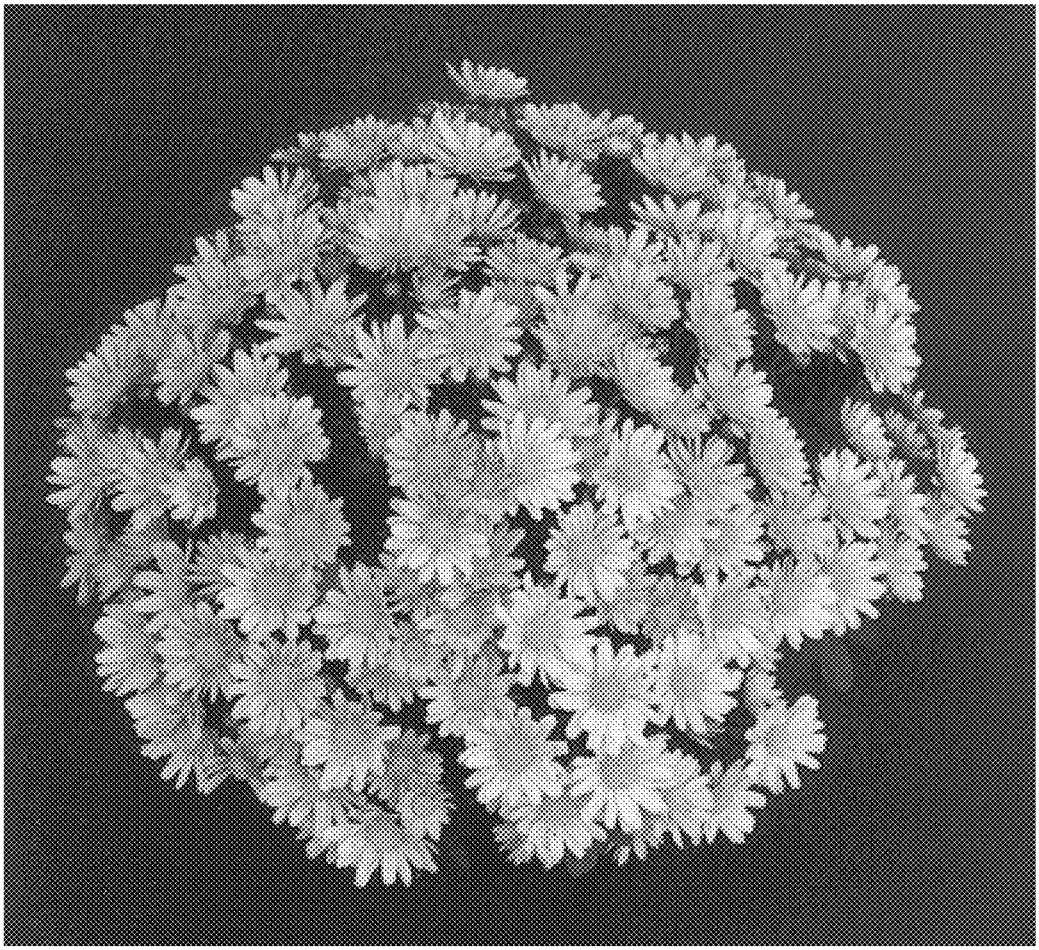

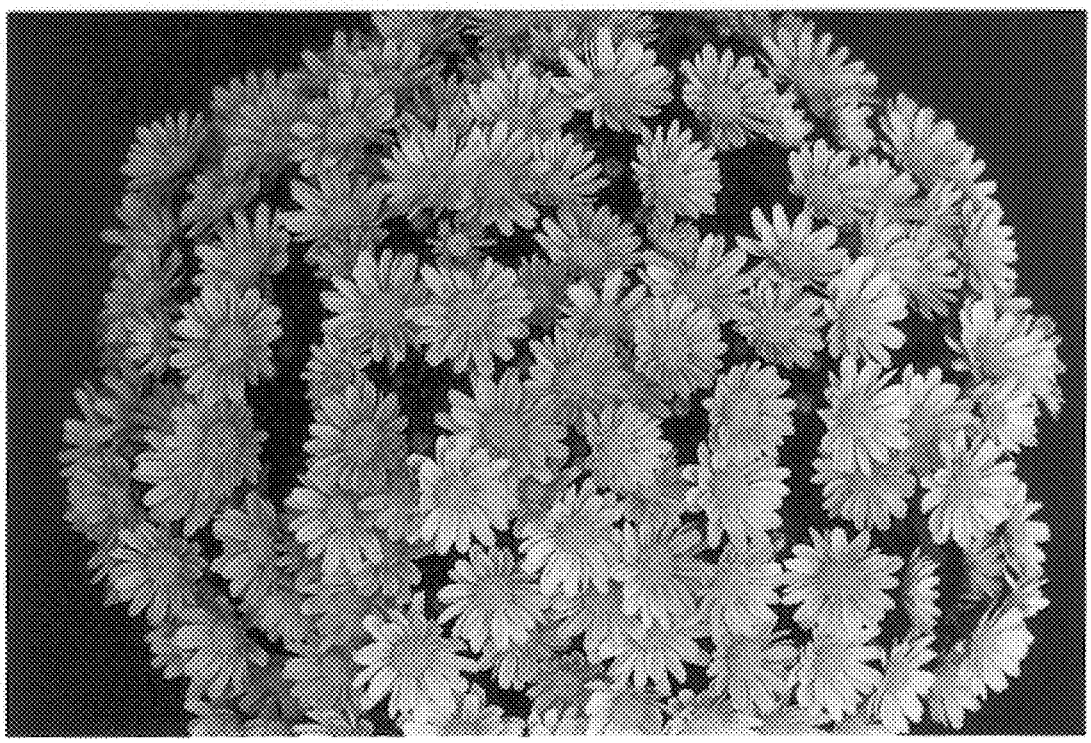
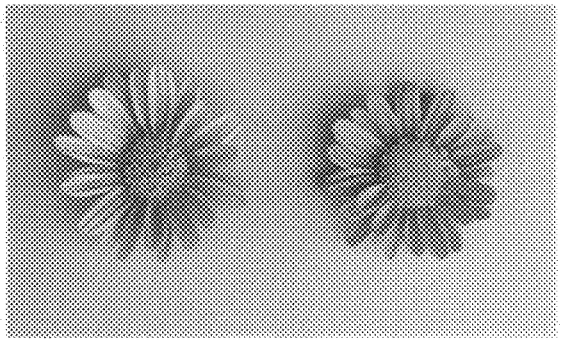

* * * * *